(12) United States Patent
Quackenbush

(10) Patent No.: US 10,016,548 B1
(45) Date of Patent: Jul. 10, 2018

(54) BREAST PUMP

(71) Applicant: Carr Lane Quackenbush, Monson, MA (US)

(72) Inventor: Carr Lane Quackenbush, Monson, MA (US)

(*) Notice: Subject to any disclaimer, the term of this patent is extended or adjusted under 35 U.S.C. 154(b) by 0 days.

(21) Appl. No.: 15/403,578

(22) Filed: Jan. 11, 2017

(51) Int. Cl.
*A61M 1/06* (2006.01)
*A61M 39/24* (2006.01)

(52) U.S. Cl.
CPC ............ *A61M 1/064* (2014.02); *A61M 39/24* (2013.01); *A61M 2205/3344* (2013.01)

(58) Field of Classification Search
CPC ........ A61M 1/064; A61M 1/06; A61M 1/062; A61M 1/066; A61M 1/068
See application file for complete search history.

(56) References Cited

U.S. PATENT DOCUMENTS

| | | | |
|---|---|---|---|
| 2,864,628 A | 12/1958 | Edleson | |
| 4,607,596 A | 8/1986 | Whittlestone et al. | |
| 4,857,051 A * | 8/1989 | Larsson | A61M 1/06 604/346 |
| 6,673,036 B1 | 1/2004 | Britto | |
| 6,749,582 B2 | 6/2004 | Britto et al. | |
| 6,840,918 B1 | 1/2005 | Britto et al. | |
| 6,887,210 B2 | 5/2005 | Quay | |
| 7,875,000 B2 | 1/2011 | Krebs et al. | |
| 7,988,661 B2 * | 8/2011 | Silver | A61M 1/066 604/74 |
| 8,052,635 B1 * | 11/2011 | Kelly | A61M 1/0037 604/74 |
| 8,118,772 B2 | 2/2012 | Dao et al. | |
| 8,216,179 B2 | 7/2012 | Bosshard et al. | |
| 8,961,454 B2 | 2/2015 | Chen | |
| 2004/0158199 A1 | 8/2004 | McKendry et al. | |
| 2006/0106334 A1 * | 5/2006 | Jordan | A61M 1/0027 604/74 |
| 2014/0121593 A1 | 5/2014 | Felber et al. | |
| 2014/0288466 A1 | 9/2014 | Alvarez et al. | |
| 2014/0378946 A1 * | 12/2014 | Thompson | A61M 1/062 604/514 |
| 2015/0065994 A1 | 3/2015 | Fridman et al. | |
| 2016/0000982 A1 | 1/2016 | Alvarez et al. | |
| 2016/0058928 A1 | 3/2016 | Nowroozi et al. | |
| 2016/0206794 A1 | 7/2016 | Makower et al. | |

FOREIGN PATENT DOCUMENTS

CA 2 240 268 A1 12/1999
WO 2004/058330 A1 7/2004

OTHER PUBLICATIONS

International Search Report for International Application No. PCT/US2017/68633 dated Mar. 19, 2018.
Written Opinion for International Application No. PCT/US2017/68633 dated Mar. 19, 2018.

* cited by examiner

*Primary Examiner* — Andrew Gilbert
*Assistant Examiner* — John Doubrava
(74) *Attorney, Agent, or Firm* — McCormick, Paulding & Huber LLP

(57) ABSTRACT

A pump apparatus and method for extracting breast milk is disclosed. The pump includes a first interface component to stimulate a Milk Ejection Reflex (MER) and a second interface component to extract breast milk. Milk is extracted through an improved method that more closely replicates the suckling of an infant.

21 Claims, 5 Drawing Sheets

BREAST PUMP

FIELD OF INVENTION

The present invention relates generally to milking and breast pump devices and, more particularly, to breast pumps for lactating females designed to mimic the natural suckling action of an infant during breast-feeding.

BACKGROUND OF THE INVENTION

Newborns and infants experience immediate and long-term benefits from breast milk feeding that are well documented. (See Cunningham A. S., Jelliffe D. B., Jelliffe E. F., Breast feeding and health in the 1980s: a global epidemiological review. Journal of Pediatrics. 1991, 118: 659-666). These benefits include providing protection against many illnesses caused by allergies, bacteria and viruses, such as stomach viruses, respiratory illnesses, ear infections, meningitis and the like. (See Fallot M. E., Boyd J. L., Oski F. A., Breast-feeding reduces incidence of hospital admissions for infection in infants. Pediatrics. 1980, 65:1121-1124). Breast milk feeding also may increase intelligence and fight obesity.

Nursing mothers may desire to impart the above-noted benefits of breast milk to their infant when the two are separated. Additionally, traditional nursing may not be possible or convenient at all times and locations. Thus, to extract breast milk to later feed to the infant, nursing mothers can use a breast pump. The extracted breast-milk can be fed to the infant using a bottle fitted with an artificial teat.

In order to remove milk, a milk ejection reflex (MER) must first occur. The mechanism to initiate an MER is not precisely understood, and is not always readily reproduced with available commercial breast pumps.

Commercial breast pumps use vacuum (negative air pressure) applied to the mother's breasts to extract milk. Such devices are typically large, loud and energy-inefficient, compromising discretion and portability. Moreover, vacuum to extract breast milk is completely different than the suckling action of the infant; in which the infant's mouth is filled only with liquid, no air. Worse still, breast pumps using only vacuum can cause significant pain or even edema in nursing mothers.

Therefore, it is desirous to provide an improved approach to breast pumps that more closely mimics the natural suckling action of the infant, is discrete in use and does not cause pain or edema.

SUMMARY OF THE INVENTION

The present invention provides a breast pump that more closely mirrors the natural suckling action of an infant, and as a result improves upon the collection of breast-milk generally associated with breast pumps.

According to the present invention, a device for extracting breast-milk from a breast, includes a funnel-shaped portion configured to receive and seal against the breast, a neck portion extending from the funnel-shaped portion including a proximal end and a distal end adapted to receive and position a nipple of the breast, a feed channel defined at the distal end of the interior of the neck portion, a one-way valve located between the feed channel and a collection container, wherein the collection container is located downstream of the one-way valve, a unitary and hermetic expandable and contractible first interface component configured to initiate an MER disposed within the device, a unitary and hermetic expandable and contractible second interface component disposed at the bottom of the neck portion toward the distal end and configured to create suction and to compress the nipple against an inner surface of the neck portion, a pump to actuate the interface components, and a valve switch to select which interface component is to be activated.

According to the present invention, a hydraulic milking machine includes a funnel-shaped breast shield, a nipple tunnel portion extending from the funnel-shaped portion including a proximal end and a downward-curving distal end, a unitary and hermetic expandable and contractible first bladder configured to initiate an MER disposed at the junction of the funnel-shaped section and neck portion, a unitary and hermetic expandable and contractible second bladder configured to compress the nipple against an upper inner surface of the neck portion, and a hydraulic pump operatively connected to the first or second bladders through a valve switch that selects which bladder is to be activated by the pump.

According to the present invention, a method of extracting milk includes providing a pumping head with a unitary and hermetic expandable and contractible first bladder and a unitary and hermetic expandable and contractible second bladder disposed within the pumping head, wherein the second bladder may contain two sections, with the first section being more resilient than the second section, providing a hydraulic pump with a valve switch, which connects the hydraulic pump to either the first bladder through the valve switch via a first tube or to the second bladder through the valve switch via a second tube, inserting a breast into the pumping head, turning the connected pumping head and hydraulic pump to an on position, initiating a stimulation phase by the hydraulic pump delivering fluid to the first bladder, expanding and contracting the first bladder against and away from the breast, then, after a pre-set period of time or sooner if the user desires, switching the valve switch to deliver fluid to the second bladder, compressing a nipple of the breast via the more resilient first section expanding and contracting more rapidly than the less resilient second section, and collecting milk excreted from the nipple via a feed channel and through the check valve.

These and other objects, features and advantages of the present invention will become apparent in light of the detailed description of embodiments thereof, as illustrated in the accompanying drawings.

As described herein, the term "vacuum" is used to connote negative air pressure, i.e. air pressure below atmospheric, whereas "suction" is used to connote negative pressure, i.e. pressure below atmospheric, in air-filled or liquid-filled systems. The term "positive pressure" is used to connote fluid pressure, air or liquid, above atmospheric pressure. "Expandable", "inflate", "inflated", "inflating", or similar terms, are used to connote an increase in size caused by applying positive fluid pressure to a bladder, i.e. pumping fluid into the bladder. "Contractible", "deflate", "deflated", "deflating", or similar terms, are used to connote a decrease in size caused by applying negative fluid pressure to a bladder, i.e. removing fluid from the bladder.

Additionally, "proximal" and "distal" are used in their medical sense and directionally with respect to the user. Thus, "distal" is farthest from the user, and the "distal portion" of the nipple is the portion drawn deepest into the pump. "Bottom," "lower" or "down" signify a direction toward the milk collection container. Conversely, "top," "upper" or "up" refer to a direction away from the milk collection container.

DETAILED DESCRIPTION OF PREFERRED EMBODIMENTS

The following descriptions of the figures will convey details of construction and operation of a breast pump in accordance with the present invention.

Figure 1A:
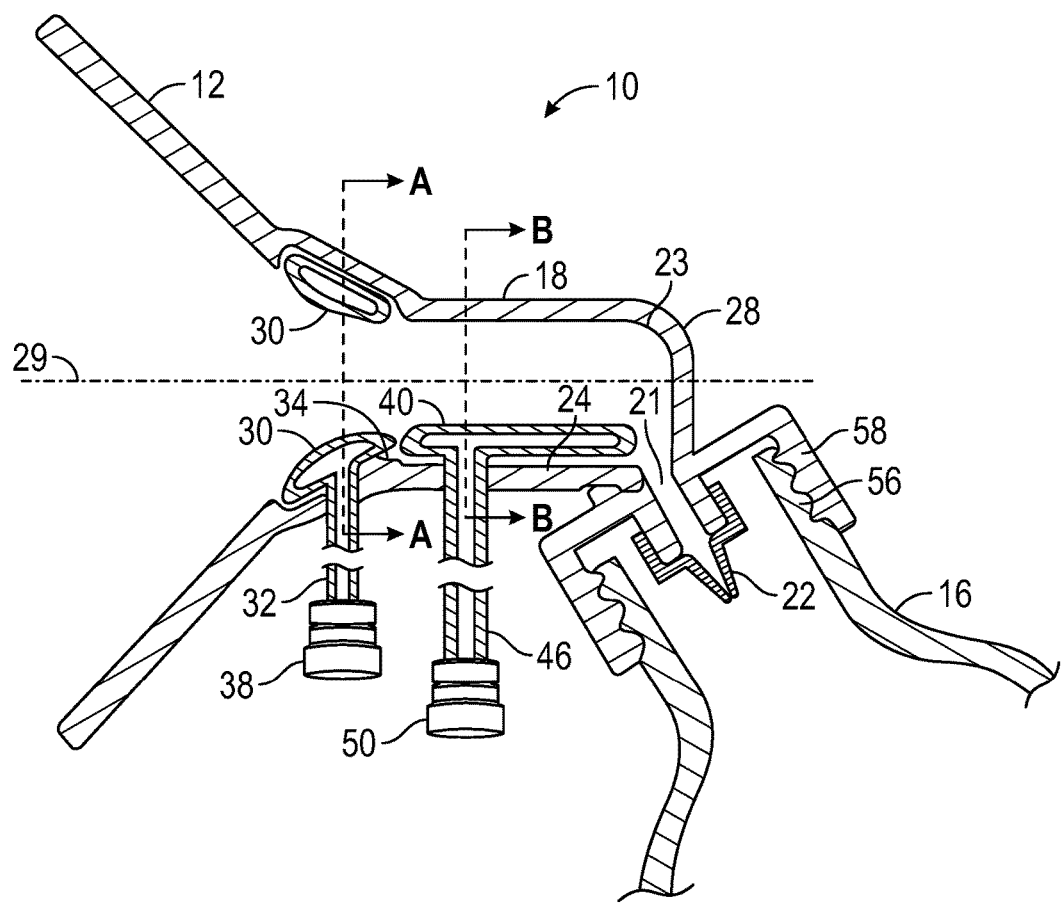
FIG. 1A is a cross section view of a breast pump head including a funnel-shaped breast shield section, a first interface component, a receiver section, a second interface component, and a milk collection container, in accordance with embodiments of the present invention.
Figure 1B:
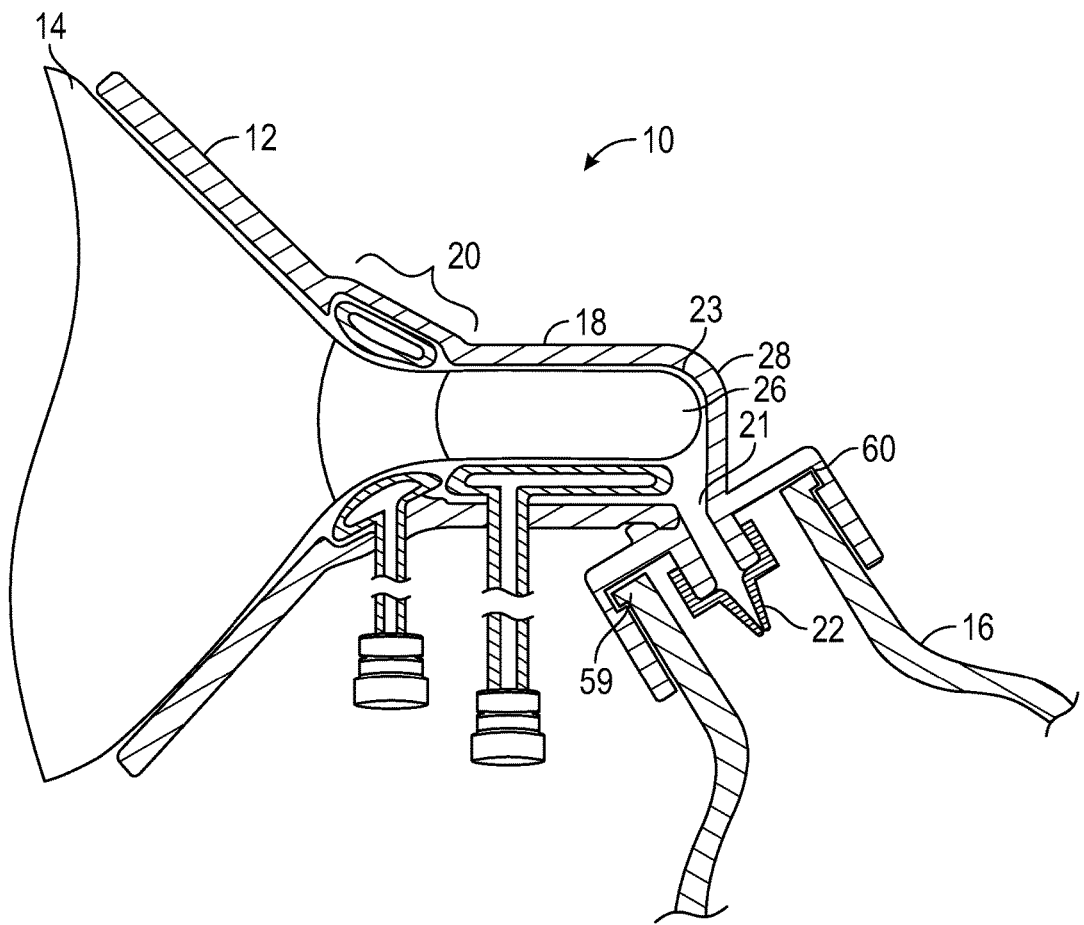
FIG. 1B is a cross section view of a breast inserted within the breast pump head of FIG. 1A, in accordance with embodiments of the present invention.

Referring to FIGS. 1A and 1B, an assembled pumping head 10 for extracting milk includes a funnel-shaped breast shield section 12 sealably connecting a breast 14 to a collection container 16 through a distally curved and hollow receiver neck section 18. As illustrated, the funnel-shaped breast shield section 12 narrows to the receiver neck section 18 through a transition section 20. The receiver neck section 18 includes a proximal end located adjacent to the transition section 20 and a distal end positioned away from the transition section 20 and the funnel-shaped breast shield section 12. Preferably, the distal end of the receiver neck section 18 is closed off so that the channel formed within the pumping head 10 feeds to a feed channel 21. In operation, when a breast 14 is placed in the pumping head 10 to extract milk, the milk will feed through this feed channel 21 then though a check valve 22 to be collected in the collection container 16.

The receiver neck section 18 includes a top surface 23 and a bottom interior surface 24 forming a hollow and nominally cylindrical area adapted to receive a nipple 26 when the user's breast is inserted into the pumping head 10. The receiver neck section 18 further includes a downward curving section 28 at its distal end. Specifically, the downward curving section 28 curves at an angle of approximately ninety to one hundred and forty degrees relative to a longitudinal axis 29 of the receiver neck section 18. The entire interior surface of the receiver section 18, including the downward curving section 28, is smooth to prevent surface imperfections from irritating the nipple 26 and shaped to not inhibit milk collection.

Figure 2A:
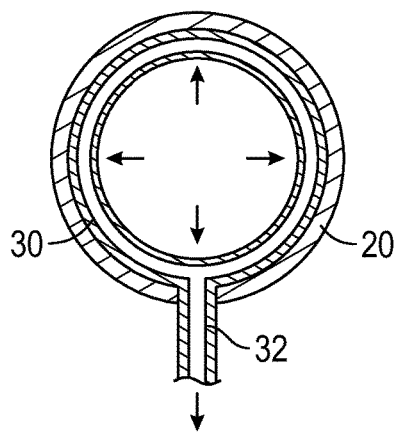
FIG. 2A is a cross section view taken across line A-A of FIG. 1A showing the receiver section and the first interface component of FIG. 1A when deflated, in accordance with embodiments of the present invention.

In embodiments of the present invention, an annular unitary and hermetic first interface component 30 configured to mechanically stimulate the breast 14 is disposed within the assembled pumping head 10. More specifically, the first interface component 30 is disposed at the transition section 20, where the breast shield section 12 meets the receiver neck section 18 and extends around the entire inner circumference/perimeter as shown in FIGS. 2(A) and (B). Additionally, the first interface component 30 is an expandable bladder filled with air or liquid for providing pulsating compression to the breast 14. In alternative embodiments, the first interface component 30 may only partially cover the circumference of the funnel-shaped breast shield section 12 and/or receiver neck section 18 forming a "C" or "U" shape. Thus, in operation, only bottom, top, side, or angled compression may be applied to an areola region of the breast 14 by the first interface component 30.

To maintain position, prevent milk leakage, and facilitate cleaning, the first interface component 30 may be bonded over the entire surface of the transition section 20 where the first interface component 30 touches the funnel breast shield section 12/receiver neck section 18 surfaces. Extending outward from the first interface component 30 and externally away from the pumping head 10 is a first tube or nozzle 32 that, as illustrated in FIG. 1A, passes through a lower interior surface 34 of the pumping head assembly 10 to a first pump tube 36 (shown in FIG. 6). In embodiments, a first leak-proof rapid disconnect 38 may be disposed between the first tube 32 and first pump tube 36.

Figure 4:
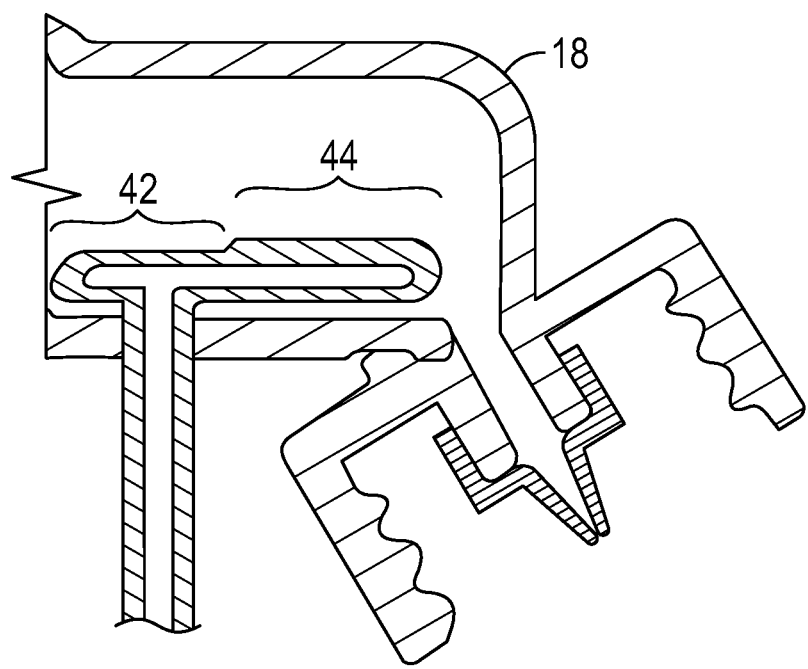
FIG. 4 is an enlarged view of the receiver section of FIG. 1A including a second interface component in accordance with another embodiment of the present invention.

Disposed along the bottom interior surface of the receiver neck section 18 is a unitary and hermetic second interface component 40 configured to inflate and deflate, and thus expand and contract within the pumping head 10. In some embodiments, the second interface component 40 is an expandable bladder filled with air or liquid and has a uniform top thickness. In other embodiments, such as shown in FIG. 4, a proximal section 42 of the top surface of the second interface component 40 is thinner than a distal section 44 of the top surface.

Figure 6:
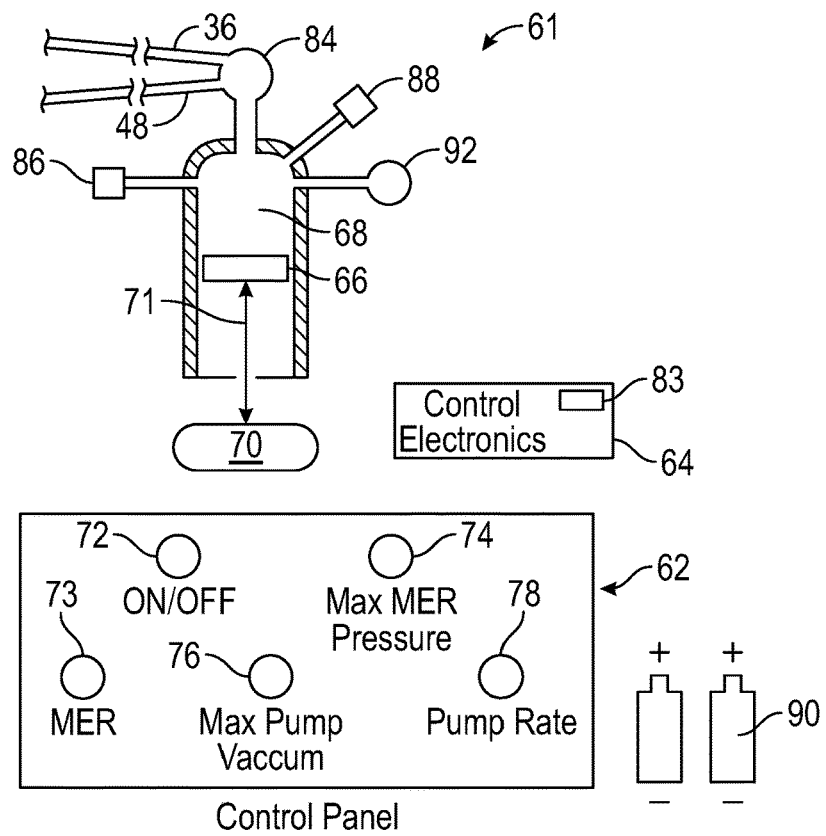
FIG. 6 is a schematic illustration of a pump including a motor, control electronics, various sensors, control elements and control panel, in accordance with embodiments of the present invention.

Referring back to FIGS. 1A and 1B, extending outward from the second interface component 40 and externally away from the pumping head 10 is a second tube or nozzle 46 that, as illustrated, passes through the lower interior surface 34 of the pumping head assembly 10 to a second pump tube 48 (shown in FIG. 6). In embodiments, a second leak-proof rapid disconnect 50 may be disposed between the second tube 46 and second pump tube 48. The two leak-proof rapid disconnects 38, 50 may be situated anywhere along the tubes 32, 46 running from the pumping head 10.

The downward curving section 28 leads into feed channel 21, which leads to check valve 22 and then into the collection container 16 which can be a bottle or bag for collecting extracted milk. Specifically, the feed channel 21 is located above the check valve 22. The check valve 22 is normally-closed, and configured to allow milk to enter the collection container 16 while preventing air from leaking into the feed channel 21 which would compromise liquid fill in the pumping head 10. In some embodiments, the check valve 22 is a duck-billed valve, although other valves are also contemplated.

The collection container 16 may contain external threads 56 corresponding to a female threaded collar 58 of the pumping head 10 for removably connecting the collection container 16. In some embodiments, the collection container contains female threads while the pumping head collar has external threads. Other means for connecting the collection container 16 to the pumping head 10 are also contemplated, such as snapping the collection container 16 with a flexibly formed top 59 into a recessed grove 60, as shown in FIG. 1B.

Figure 2B:
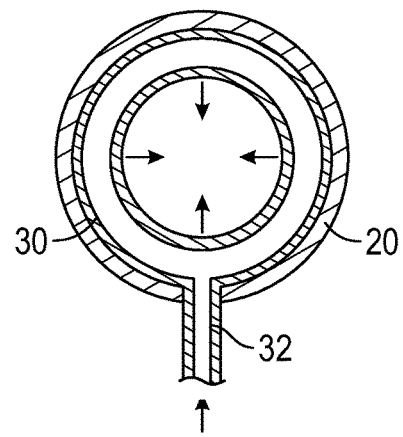
FIG. 2B is a cross section view taken across line A-A of FIG. 1A showing the receiver section and the first interface component of FIG. 1A when inflated, in accordance with embodiments of the present invention.

Referring to FIGS. 2A and 2B, a cross-section of the transition section 20 across line A-A in FIG. 1A is shown.

The overall cross-section of the transition section 20 is substantially circular as the funnel-shaped shield section 12 narrows to the hollow receiver neck section 18. As discussed in connection with FIG. 1A, the annular first interface component 30 extends completely or partially around the inner circumference/perimeter of the funnel-shaped shield section 12, transition section 20 and/or receiver section 18. When the first interface component 30 is deflated, the aperture through the funnel-shaped shield section 12, transition section 20 and/or receiver section 18 is larger than when the first interface component 30 is inflated.

Figure 3:
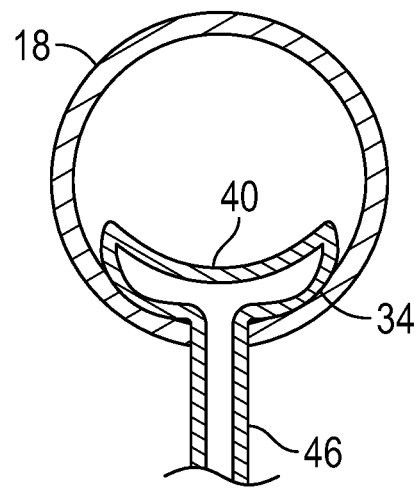
FIG. 3 is a cross section view taken across line B-B of FIG. 1A showing the receiver section and the deflated second interface component of FIG. 1A, in accordance with embodiments of the present invention.

Referring to FIG. 3, a cross-section of the receiver neck section 18 across line B-B in FIG. 1A is shown with the second interface component substantially deflated.

The overall cross-section of the receiver neck section 18 is substantially round such that the neck section 18 generally forms a cylindrical tube, although it may have other shapes, for example oval. For positioning, to prevent milk leakage and to facilitate cleaning, the second interface component 40 may be bonded where it touches the lower interior surface 34 and generally extend along the bottom interior surface 24 of the tubular neck section 18. In embodiments, and as pictured in FIG. 3, a fully deflated second interface component 40 maintains the substantially round internal cross-section of the receiver neck section 18. In alternative embodiments, when inflated the second interface component 40 may sufficiently occupy the interior distal portion of the receiver neck section 18 such that compression may be applied to the nipple 26 by the second interface component 40 so that the nipple 26 is completely compressed against the top interior of the neck section 18. These inflations and deflations of the second interface component 40 are intended to mimic the natural suckling action of an infant.

Referring to FIG. 4, an enlarged view of the receiver neck section 18 of FIG. 1A including a second interface component 40 in accordance with an embodiment of the present invention is shown. The proximal section 42 of the top surface of the second interface component 40 is thinner than the distal section 44 of the top surface. The thinner proximal section 42 allows it to stretch more easily than the thicker distal section 44 which is stiffer and so more difficult to stretch. Thus when the second interface component 40 is expanding, the proximal section 42 will rise in advance of the distal section 44. When the second interface component 40 is contracting, the proximal section 42 will remain in an elevated position longer relative to the distal section 44. This operation is pictured in FIGS. 5A, 5B and 5C.

Figure 5A:
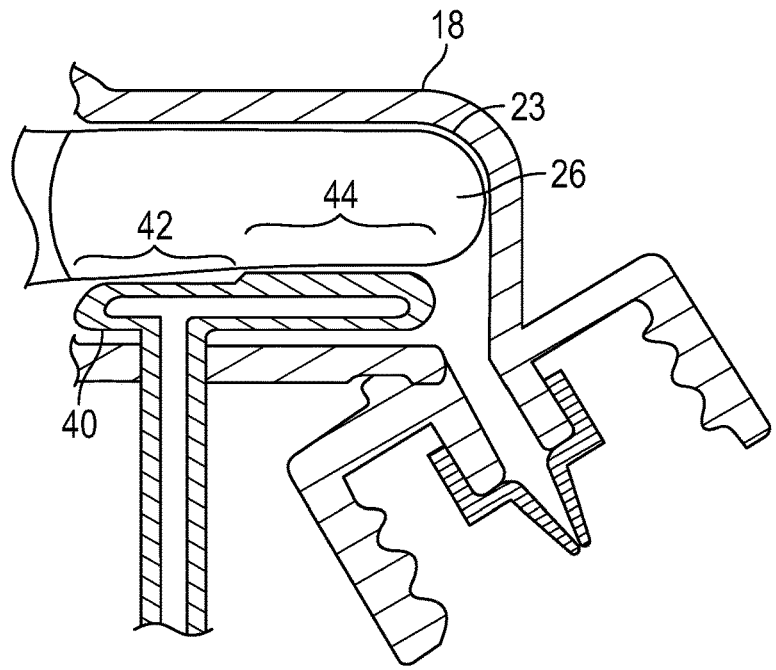
FIG. 5A is a cross section view of the second interface component of FIG. 4 in a fully deflated initial position, in accordance with embodiments of the present invention.
Figure 5B:
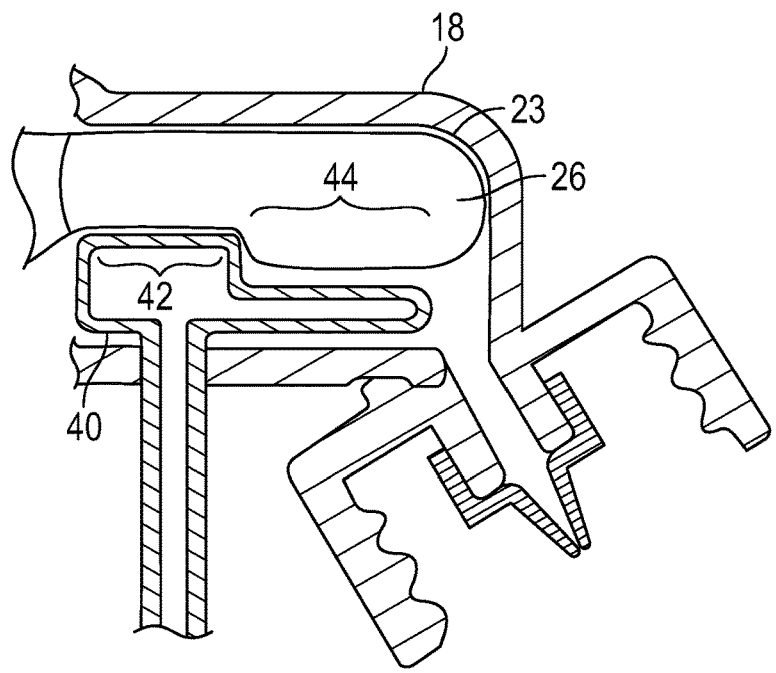
FIG. 5B is a cross section view of the second interface component of FIG. 4 at a slightly inflated configuration, in accordance with embodiments of the present invention.
Figure 5C:
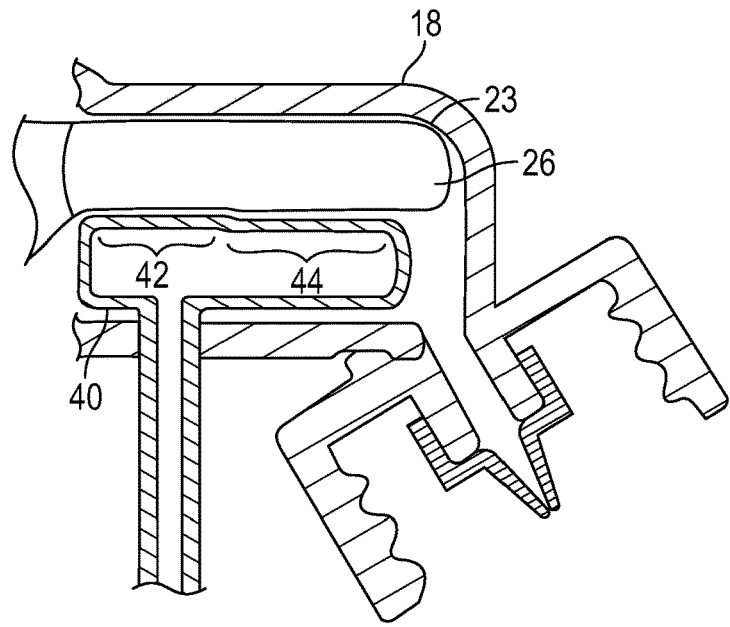
FIG. 5C is a cross section view of the second interface component of FIG. 4 in a fully inflated position, in accordance with embodiments of the present invention.

Referring to FIG. 5A, in an initial position, the second interface component 40 is fully deflated. Referring to FIG. 5B, in a slightly inflated configuration, the proximal section 42 of the second interface component 40 is expanded and moves up to asymmetrically compress the nipple 26. Referring to FIG. 5C, in a fully inflated position, the distal section 44 of the second interface component 40 is now fully up, uniformly compressing the nipple 26. When deflating from the fully inflated position of FIG. 5C, the second interface component 40 contracts asymmetrically to the slightly inflated position shown in FIG. 5B.

Referring to FIG. 6, a pump 61 actuated by a control panel 62 through a series of control electronics 64 is shown. The pump 61 includes a piston 66 housed within a cylinder 68. A motor 70 drives the piston 66 by a propulsion mechanism 71. The propulsion mechanism 71 can be, for example, lead screws, a rack and pinion system, a crank and axle system or other type of mechanism capable of extending and retracting the piston 66. In preferred embodiments of the present invention, the pump 61 is a hydraulic pump. In alternative embodiments, the pump 61 can be a pneumatic pump.

The pump 61 shown in FIG. 6 is a piston 66 in cylinder 68 although any positive displacement pump will suffice e.g. a diaphragm pump, peristaltic pump etc.

The control panel 62 includes an on/off switch 72, an MER button 73, a maximum MER pressure selector 74 and a maximum pump suction selector 76. The on/off switch 72 is configured to initiate the pump 61 through a series of control electronics 64 controlled by a control logic 83.

The pump 61 further includes an electrically actuated valve switch 84 to direct pump suction or pressure from the cylinder 68 to the first interface component 30 via the first pump tube 36 or to the second interface component 40 via the second pump tube 48. A reservoir 86 provides make-up liquid or air to the cylinder 68 of the pump 61. Similar to hydraulic and automotive braking systems, the pump 61 may further include an air bleed 88 to exhaust air in the case of a liquid-filled system. Alternating current (AC) or batteries 90 can provide power to the pump 61.

Position sensors, stepper motors, and other suitable sensors and electronics may be included for controlling suction levels, suction rates, pumping frequency and the like, without departing from the scope of the present invention.

In embodiments, the pump 61 also includes a pressure sensor 92 connected to the cylinder 68 and adapted to report real-time system pressure to the control electronics 64.

In operation, the breast 14 is inserted into the breast shield section 12 and the nipple 26 extends into the receiver neck section 18. The second interface component 40, which was fully deflated at the end of the last pumping session during the shutdown sequence, allows the nipple 26 to enter the nipple tunnel/receiver neck section 18 unimpeded. The location of the first interface component 30 and/or the funnel shape of the shield section 12 establish a seal around the breast 14.

Next, the pump 61 is switched on with the on/off switch 72 disposed on the control panel 62. The control electronics 64 start an initiation sequence by switching the valve switch 84 to the second interface component 40.

The activated pump 61 begins to cycle, alternately inflating and deflating the second interface component 40. With each deflation, suction in the receiver neck section 18 increases, pulling/elongating the nipple 26. With each inflation of the second interface component 40, air in the receiver neck section 18 is squeezed out through the check valve 22.

The initiation sequence continues until the nipple 26 contacts (i.e. is seated against) the downward curving section 28. After air has been exhausted the feed channel 21 is completely filled with liquid. In this regard, an important function of the one-way check valve 22 is to maintain separation between the liquid-filled feed channel 21 and the air-filled collection container 16 and, thereby, to maintain liquid fill in the pumping head 10.

At this point, the pressure sensor 92 will detect a sharp increase in suction when the nipple 26 seats against the downward curving section 28 because the volume created by the downward motion of the second interface component 40 will no longer be absorbed by the nipple 26 pulling/elongating to fill that created volume. Upon detection, the pressure sensor 92 reports the abrupt suction increase to the control electronics 64 and control logic 83. The control logic 83 and control electronics 64 are pre-set to then switch the valve switch 84 to the first interface component 30 in response to this abrupt suction change report.

Next, the pump 61 and first interface component 30 initiate a stimulation phase by alternately expanding the first interface component 30 against the areola section of the breast 14 to cause compression and massage to that region. Such compression may be, for example, one hundred to one hundred forty compressions per minute, preferably one hundred twenty compressions per minute for approximately two minutes.

The first interface component 30 can be a bladder or other expandable membrane capable of expanding and contracting. In embodiments, the first interface component 30 is positioned such that the areolar region is contacted completely around its circumference by the first interface component 30. In some embodiments, only the top and bottom of the areolar region are contacted. In other embodiments, only the lower region of the areolar is contacted. Further, it is understood that the first interface component 30 can be disposed anywhere within the shield 12 or receiver neck section 18, but preferably at transition region 20 and be bonded to some or the entire inner surface of the pumping head 10, provided the first interface component 30 or other bladder substantially performs the functions described herein.

The user may select the maximum MER pressure using knob 74 disposed on the control panel 62. A pressure feed back signal from the pressure sensor 92 allows for further fine-tuning pressure by the user. Inflation/deflation profiles are pre-programed.

The stimulation phase ends after expiration of a set time (e.g. two minutes) or by pressing the MER button 73. After the stimulation phase, an MER has likely been initiated.

The MER button 73 is a toggle, which may be selected any time during the pumping session causing a change from MER stimulation to milk extraction or vice versa.

This initiation sequence may alternatively be performed in reverse. That is, the first interface component 30 may operate first followed after two minutes or sooner if selected by the user, by the second interface component.

Additionally, the first interface component 30 and/or the second interface component 40 can be run under hot water to heat the components and any fluid contained therein. The warmth can also facilitate an MER.

After the preset time period or by the user pressing the MER button 73, the control electronics 64 cause the first interface component 30 to deflate, then cause the valve switch 84 to change back to the second interface component 40. The control electronics 64 then cause the second interface component 40 to inflate and deflate.

When the second interface component 40 begins to deflate, it moves down more creating volume around and in front of the nipple 26. The volume created by the deflation pulls the check valve 22 closed and creates suction, which extracts milk into the feed channel 21. More specifically, the extracted milk is drawn into the "suction chamber," a volume bounded by the nipple 26, the downward curving section 28, the distal end of the second interface component 40 and the check valve 22. This milk extraction process utilizing suction in a liquid-filled system mimics the natural suckling action of an infant.

When the second interface component 40 inflates two events occur. First, the nipple is compressed against the top surface 23 and/or downward curving section 28 of the receiver neck section squeezing the nipple tissues and thereby preventing edema, an accumulation of fluid in the tissues. Edema is a common cause of pain during breast pumping with conventional air-filled breast pumps. This prevention of edema by compression is analogous to the use of compression socks to control foot swelling. Second, as the second interface component 40 inflates, it moves up causing a change from negative to positive pressure in the suction chamber. This positive pressure pushes the extracted milk through the check valve 22 and into the collection container 16.

In some embodiments, the top surface of the second interface component 40 has a uniform thickness as shown in FIGS. 1A and 1B. In this case it inflates uniformly.

In alternative embodiments, the proximal section 42 of the top surface of the second interface component 40 is thinner than the distal section 44, as shown in FIG. 4. Accordingly, when inflated, the more resilient proximal section 42 will rise in advance of the distal section 44. Conversely, when deflating, the proximal section 42 will fall later than the distal section 44. Thus, the proximal section 42 would lead on inflation and lag on deflation relative to the distal section 44.

The pump 61 actuates the piston 66 creating a pumping cycle of between forty and eighty, preferably about sixty cycles per minute. Maximum suction for the second interface component 40 can be controlled through feedback from the pressure sensor 92 and the separate maximum pump suction selector knob 76 disposed on the control panel 62. The suction rate curve to reach maximum suction caused by deflation of the second interface component 40 is pre-programed. Inflation/deflation frequency of the second interface component 40 is also pre-programmed or may be linked so that, for example, changing suction by knob 76 changes frequency in a pre-programmed fashion or frequency may be controlled by a separate knob 78 on the control panel 62.

When the pumping session is complete, the on/off switch 72 on control panel 62 is switched to the off position and a shutdown sequence is initiated. The valve switch 84 remains switched to the second interface component 40 until the second interface component 40 is fully deflated. Then the valve switch 84 switches to the first interface component 30, and fully deflates it. Control electronics 64 then switch off the pump 61 and the unit is fully off.

The user can insert a finger into the receiver neck section 18 and break the residual vacuum from the breast 14 and the shield section 12.

Milk collected in the collection container 16 can be fed to an infant or stored for future use.

The leak-proof rapid disconnects 38, 50 allow the pumping head 10 to be separated from the tubes/nozzles coming from the pump 36, 48 without losing liquid from either part. After the rapid disconnects 38, 50 are separated; the pumping head 10 can be cleaned. Alternatively, there may be no disconnects and the pumping head 10 can be cleaned while still connected to the pump.

Additionally, the check valve 22 can be removed to facilitate cleaning the pumping head 10. Any residual milk can be removed from the interior of the funnel 12 and the receiver neck section 18 via a brush with soap, detergent and warm water.

One advantage of the bonding of the first interface component 30 and/or second interface component 40 is that the bonding holds the bladder in position, and creates a liquid-tight seal. Thus, the pumping head 10 of the present invention avoids breast milk leakage out of the receiver section and prevents extracted milk from collecting under the bladder. This feature also facilitates cleaning of the pumping head assembly 10.

One advantage of the resilient proximal section 42 and second interface component 40 is that the rise and fall motion is akin to a rolling action, allowing the proximal section 42 to "pin" the nipple 26 in place, restricting the nipple's elastic retraction away from the downward curving section 28 of the receiver neck section 18, when the second interface component is deflating. Consequently, embodiments of the present invention may further limit ineffective nipple 26 motion that would dissipate suction.

One advantage of the second interface component 40 is to compress the nipple 26 against the top surface 23 and/or downward curving section 28 with enough force to prevent the pooling of blood and other fluids in the nipple 26 tissues. The compression helps prevent edema—a painful condition caused by other commercially available breast pumps.

In embodiments solely using liquid to expand and contract the first interface component 30 and second interface component 40, the pump 61 may deliver quicker and more precise actions and possibly with stronger force than can be achieved with air-filled systems.

Another advantage of the hydraulic embodiments is that the pump 61 may be physically smaller and more discrete, as the hydraulic embodiments pump will pump less than five percent the volume per cycle when compared to air-driven pumps. Further, a less "hard working" pump can be quieter and more energy efficient, improving battery life, a great aid to mobility and ease of use.

Another advantage of the pumping head 10 of the present invention is that the second interface component upward motion reduces volume in the pumping cavity (i.e. receiver neck section 18) and forces extracted milk through the check valve 22 and into the collection container 16. Most commercial air-driven breast pumps can develop vacuum only with no ability to create positive pressure, and so they depend only on weight of the extracted breast milk to push it through the check valve. This method does not work reliably, and milk often backs up into the vacuum line, sometimes contaminating the pump, and creating a very unhygienic condition.

In another embodiment the entire interior surface of pumping head 10 may be coated with a highly elastic material to form an adherent membrane which covers the inside of funnel shield section 12, neck section 18, feed channel 21 and both the first interface component 30 and second interface component 40. Such an elastic membrane allows full and unrestricted expansion and contraction functioning of both bladders while preventing milk collection in small spaces inside the pumping head. This configuration will ease cleaning, Additionally, the features of the present invention may also be used for milking machines. Specifically, the above described method and pumping head 10 may be used for the milking of animals.

Although this invention has been shown and described with respect to the detailed embodiments thereof, it will be understood by those skilled in the art that various changes in form and detail thereof may be made without departing from the spirit and scope of the invention.

It is noted that the Figures are to be taken as an illustrative example only, and are not to scale.

Additionally, it is also to be understood that the terminology used if for the purpose of describing particular embodiments only, and is not intended to limit the scope of the claims of the present invention.

What is claimed is:

1. A device for extracting breast-milk from a breast, said device comprising:
    an external shell including:
        a funnel-shaped portion configured to receive and seal against the breast;
        a neck portion extending from the funnel-shaped portion including a proximal end and a distal end adapted to receive and position a nipple of the breast, and
        a feed channel defined at the distal end of an interior of the neck portion;
    a unitary hermetic expandable and contractible first interface component configured to initiate a milk ejection reflex (MER) disposed within the device; and
    a unitary hermetic expandable and contractible second interface component extending into the neck portion;
    wherein the second interface component is configured to expand under applied positive pressure above atmospheric pressure to compress the nipple against an opposing solid surface of the neck portion to control nipple edema, and
    wherein the second interface component is configured to contract under applied negative pressure below atmospheric pressure to create a volume external to the second interface component, around and in front of the nipple, to create suction and extract breast milk.

2. The device of claim 1, wherein the second interface component is disposed at a lower interior surface of the neck portion.

3. The device of claim 1, wherein the second interface component is configured to prevent nipple from retracting while inflating.

4. The device of claim 1, wherein the first interface component expands and contracts at a rate between one hundred and one hundred forty cycles per minute.

5. The device of claim 1, wherein the second interface component expands and contracts uniformly and at a rate between forty and eighty cycles per minute.

6. The device of claim 1, wherein air fills the expandable and contractible first interface component and the second expandable and contractible interface component.

7. The device of claim 1, wherein liquid fills the expandable and contractible first interface component and the second expandable and contractible interface component.

8. The device of claim 1 further including a collection container to receive milk.

9. The device of claim 8, further including a one-way valve disposed between the neck portion and the collection container to prevent air leakage from the collection container into the liquid-filled feed channel.

10. The device of claim 1, wherein the feed channel curves between about a ninety and a one hundred forty degree angle relative to a longitudinal axis of the neck portion.

11. The device of claim 3, wherein the second interface component includes a proximal surface and a distal top surface, wherein the proximal top surface is more resilient than the distal top surface; and wherein the proximal top surface rises in advance of the distal surface when expanding and falls later than the distal surface when contracting.

12. The device of claim 1, wherein a tube connected to the first interface component passes through the external shell.

13. The device of claim 1, wherein a tube connected to the second interface component passes through the external shell.

14. A hydraulic milking machine comprising:
an external shell including:
- a funnel-shaped portion configured to receive and seal against a breast;
- a neck portion extending from the funnel-shaped portion including a proximal end and a distal end adapted to receive and position a nipple of the breast; and
- a feed channel defined at the distal end of an interior of the neck portion;

a unitary hermetic expandable and contractible first bladder configured to initiate a milk ejection reflex (MER) disposed at the junction of the funnel-shaped section and neck portion;

a unitary hermetic expandable and contractible second bladder; and a hydraulic pump operatively connected through a selector valve to the first or second bladders;

wherein the second bladder is configured to expand under applied positive pressure above atmospheric pressure to compress the nipple against an opposing surface of the neck portion to control nipple edema, and wherein the second bladder is configured to contract under applied negative pressure below atmospheric pressure to create a volume external to the second bladder, around and in front of the nipple, to create suction and extract breast milk.

15. The milking machine of claim 14, wherein the first bladder, the hydraulic pump, and tubing connecting the first bladder and the hydraulic pump, are all filled with liquid.

16. The milking machine of claim 14, wherein the second bladder, the hydraulic pump, and tubing connecting the second bladder and the hydraulic pump, are all filled with liquid.

17. The milking machine of claim 15, wherein the liquid-filled first bladder is connected by the liquid-filled tubing to the hydraulic pump via a leak proof disconnect.

18. The milking machine of claim 16, wherein the liquid-filled second bladder is connected by liquid-filled tubing to the liquid-filled hydraulic pump via a leak proof disconnect.

19. The milking machine of claim 14, wherein the first and second unitary hermetic bladders are fabricated from silicone rubber.

20. The milking machine of claim 15, wherein the tubing connecting the first bladder and the hydraulic pump passes through the external shell.

21. The milking machine of claim 15, wherein the tubing connecting the second bladder and the hydraulic pump passes through the external shell.

* * * * *